(12) United States Patent
Bastian et al.

(10) Patent No.: US 8,445,493 B2
(45) Date of Patent: May 21, 2013

(54) TETRASUBSTITUTED PYRIDAZINES HEDGEHOG PATHWAY ANTAGONISTS

(75) Inventors: Jolie Anne Bastian, Indianapolis, IN (US); Julia Marie Clay, Zionsville, IN (US); Takako Wilson (nee Takakuwa), Indianapolis, IN (US); Michelle Lee Thompson, Greenwood, IN (US); Daniel Jon Sall, Greenwood, IN (US); Philip Arthur Hipskind, New Palestine, IN (US)

(73) Assignee: Eli Lilly and Company, Indianapolis, IN (US)

( * ) Notice: Subject to any disclaimer, the term of this patent is extended or adjusted under 35 U.S.C. 154(b) by 111 days.

(21) Appl. No.: 13/122,225

(22) PCT Filed: Nov. 9, 2009

(86) PCT No.: PCT/US2009/063696
§ 371 (c)(1),
(2), (4) Date: Apr. 1, 2011

(87) PCT Pub. No.: WO2010/056620
PCT Pub. Date: May 20, 2010

(65) Prior Publication Data
US 2011/0178093 A1 Jul. 21, 2011

Related U.S. Application Data

(60) Provisional application No. 61/115,362, filed on Nov. 17, 2008.

(51) Int. Cl.
*C07D 401/04* (2006.01)
*A61K 31/501* (2006.01)
*A61P 35/00* (2006.01)

(52) U.S. Cl.
USPC ..................... 514/252.02; 544/238

(58) Field of Classification Search ............. 514/252.02; 544/238
See application file for complete search history.

(56) References Cited

U.S. PATENT DOCUMENTS

| 3,753,988 | A | 8/1973 | Rodway et al. |
| 5,985,878 | A | 11/1999 | Stokbroekx et al. |
| 6,432,970 | B2 | 8/2002 | Beachy et al. |
| 2009/0048259 | A1 | 2/2009 | Austin et al. |
| 2010/0324048 | A1 | 12/2010 | Hipskind |
| 2011/0046143 | A1 | 2/2011 | Hipskind |

FOREIGN PATENT DOCUMENTS

| WO | WO 97/26258 A1 | 7/1997 |
| WO | WO 99/52534 A1 | 10/1999 |
| WO | WO 00/74706 A1 | 12/2000 |
| WO | WO 03/088970 A2 | 10/2003 |
| WO | WO 2004/020599 A2 | 3/2004 |
| WO | 2005/033288 A2 | 4/2005 |
| WO | WO 2005/080378 A1 | 9/2005 |
| WO | WO 2006/004589 A2 | 1/2006 |
| WO | WO 2006/028958 A2 | 3/2006 |
| WO | WO 2008/028689 A1 | 3/2008 |
| WO | WO 2008/110611 A1 | 9/2008 |
| WO | WO 2009/002469 A1 | 12/2008 |
| WO | WO 2009/035568 A1 | 3/2009 |
| WO | WO 2009/134574 A2 | 11/2009 |
| WO | WO 2010/007120 A1 | 1/2010 |
| WO | WO 2010/056588 A1 | 5/2010 |
| WO | WO 2010/062507 A1 | 6/2010 |

OTHER PUBLICATIONS

Merchant, et al., Clin. Cancer Res., 16(12), Jun. 15, 2010.*
Scales, et al., Trends in Pharmacological Sciences, 30, 6, 2009, 303-312.*
Lin, et al., PLoS ONE, Dec. 2010, 5, 12, e15262.*
Frank-Kamenetsky, M., et al., "Small-molecular modulators of Hedgehog signaling: identification and characterization of Smoothened agonists and antagonists," Journal of Biolology vol. 1, Issue 2, Article 10, pp. 10.1-10.19 (2002).
Lee, J., et al., "A small-muleclar antagonist of the Hedgehog signaling pathway," ChemBioChem, vol. 8, pp. 1916-1919 (2007).
McMahon, G., VEGF Receptor Signaling in Turnor Angiogenisis. The Oncologist, 5(suppl 1):3-10 (2000). [www.TheOncologist.com].
Tremblay, M., et al., "Semisynthetic cyclopamine analogues as potent and orally bioavailable Hedgehog pathway antagonists," J. Med. Chem., vol. 51, pp. 6646-6649 (2008).
Tremblay, M., et al., "Recent patents for Hedgehog pathway inhibitors for the treatment of malignancy," Expert Opin. Ther. Patents 19(8):1039-1056 (2009).
Pinedo, et al., "Translational Research: The Role of VEGF in Tumor Angiogenesis," The Oncologist, 5(suppl 1):1-2 (2000) [www.TheOncologist.com].

* cited by examiner

*Primary Examiner* — Susanna Moore
*Assistant Examiner* — Cecilia M Jaisle
(74) *Attorney, Agent, or Firm* — Danica Hostettler; John C. Demeter

(57) ABSTRACT

The present invention provides novel tetrasubstituted pyridazine hedgehog pathway antagonists useful in the treatment of cancer.

9 Claims, No Drawings

TETRASUBSTITUTED PYRIDAZINES HEDGEHOG PATHWAY ANTAGONISTS

This application is a national phase application under 35 U.S.C. Section 371 of PCT/US2009/063696, filed Nov. 9, 2009, which claims the benefit under 35 U.S.C. Section 119(e) of U.S. provisional patent application 61/115,362, filed Nov. 17, 2008.

The present invention relates to Hedgehog pathway antagonists and, more specifically, to novel tetrasubstituted pyridazines and therapeutic use thereof. The Hedgehog (Hh) signaling pathway plays an important role in embryonic pattern formation and adult tissue maintenance by directing cell differentiation and proliferation. The Hedgehog (Hh) protein family, which includes Sonic Hedgehog (Shh), Indian Hedgehog (Ihh), and Desert Hedgehog (Dhh) are secreted glycoproteins that undergo post-translational modifications, including autocatalytic cleavage and coupling of cholesterol to the amino-terminal peptide to form the fragment that possesses signaling activity. Hh binds to the twelve-pass trans-membrane protein Ptch (Ptch1 and Ptch2), thereby alleviating Ptch-mediated suppression of Smoothened (Smo). Smo activation triggers a series of intracellular events culminating in the stabilization of the Gli transcription factors (Gli1, Gli2, and Gli3) and the expression of Gli-dependent genes that are responsible for cell proliferation, cell survival, angiogenesis and invasion.

Hh signaling has recently attracted considerable interest based on the discovery that aberrant activation of Shh signaling leads to the formation of various tumors, e.g., pancreatic cancer, medulloblastoma, basal cell carcinoma, small cell lung cancer, and prostate cancer. Several Hh antagonists have been reported in the art, such as the steroidal alkaloid compound IP-609; the aminoproline compound CUR61414; and the 2,4-disubstituted thiazole compound JK18. WO2005033288 discloses certain 1,4-disubstituted phthalazine compounds asserted to be hedgehog antagonists. Similarly, WO2008110611 discloses certain 1,4 disubstituted phthalazine compounds related to the diagnosis and treatment of pathologies related to the hedgehog pathway.

There still exists a need for potent hedgehog pathway inhibitors, particularly those having desirable pharmacodynamic, pharmacokinetic and toxicology profiles. The present invention provides novel tetrasubstituted pyridazines that are potent antagonists of this pathway.

The present invention provides a compound of the following formula:

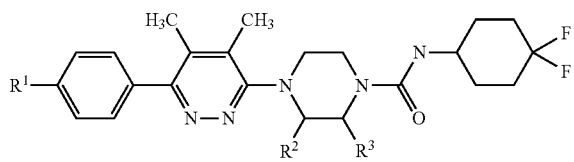

wherein:
$R^1$ is hydrogen, fluoro or cyano; and
$R^2$ and $R^3$ are independently methyl or hydrogen;
or a pharmaceutically acceptable salt thereof.

It will be understood by the skilled artisan that the compounds of the present invention comprise a tertiary amine moiety and are capable of reaction with a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts, "*Journal of Pharmaceutical Sciences*, Vol 66, No. 1, January 1977.

Specific embodiments of the invention include compounds of Formula I, or a pharmaceutically acceptable salt thereof, wherein:
(a) $R^1$ is hydrogen; and
(b) The compound of claim 1 or 2 wherein one of $R^2$ and $R^3$ is hydrogen and the other is methyl.

The present invention also provides a pharmaceutical composition comprising a compound of Formula I, or a pharmaceutically acceptable salt thereof, in combination with a pharmaceutically acceptable excipient, carrier or diluent.

The compounds of the present invention are preferably formulated as pharmaceutical compositions administered by a variety of routes. Preferably, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

The present invention also provides a method of treating brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma in a patient comprising administering to a patient in need of such treatment an effective amount of a compound of Formula I, or a pharmaceutically acceptable salt thereof.

It will be understood that the amount of the compound actually administered will be determined by a physician under the relevant circumstances, including the condition to be treated, the chosen route of administration, the actual compound or compounds administered, the age, weight, and response of the individual patient, and the severity of the patient's symptoms. Dosages per day normally fall within the range of about 0.1 to about 5 mg/kg of body weight. In some instances dosage levels below the lower limit of the aforesaid range may be more than adequate, while in other cases still larger doses may be employed. Therefore, the above dosage range is not intended to limit the scope of the invention in any way. This invention also provides a compound of Formula I, or a pharmaceutically acceptable salt thereof, for use as a medicament.

Additionally, this invention provides use of a compound of Formula I, or a pharmaceutically acceptable salt thereof, in the manufacture of a medicament for treating cancer. In particular, the cancer is selected from the group consisting of brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma.

Furthermore, this invention provides a pharmaceutical composition comprising a compound of Formula I, or a pharmaceutically acceptable salt thereof, as an active ingredient for treating brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma.

The compounds of Formula I, or salts thereof, may be prepared by a variety of procedures known in the art, as well as those described in the Schemes, Preparations, and Examples below. The specific synthetic steps for each of the routes described may be combined in different ways, or in conjunction with steps from different schemes, to prepare compounds of Formula I, or salts thereof.

"HOBT" refers to 1-hydroxybenzotriazole hydrate; "DMF" refers to N,N-dimethylformamide; "DMSO" refers to methylsulfoxide; "EtOAc" refers to ethyl acetate; "MeOH" refers to methanol; "TFA" refers to trifluoroacetic acid; "SCX" refers to strong cation exchange; and "IC$_{50}$" refers to the concentration of an agent that produces 50% of the maximal inhibitory response possible for that agent.

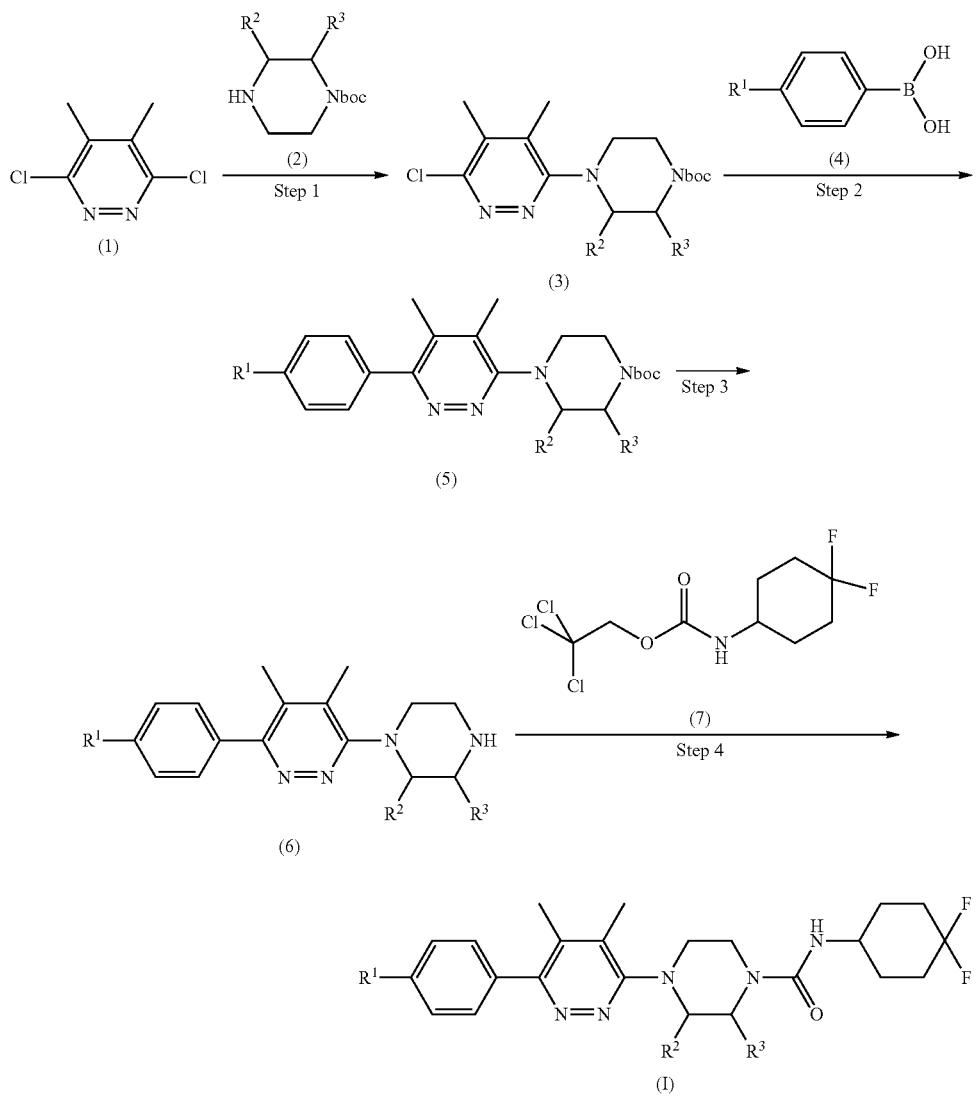

Scheme 1

The substituents, unless otherwise indicated, are as previously defined. The reagents and starting materials are generally readily available to one of ordinary skill in the art. Others may be made by standard techniques of organic and heterocyclic chemistry, techniques which are analogous to the syntheses of known structurally-similar compounds, and the procedures described in the Preparations and Examples which follow including any novel procedures.

As used herein, the following terms have the meanings indicated: "boc" or "t-boc" refers to tert-butoxycarbonyl; "EDCI" refers to 1-(3-dimethylaminopropyl)-3-ethylcarbodiimide hydrochloride; "Et$_2$O" refers to diethyl ether;

A compound of Formula I can be prepared in accordance with reactions as depicted in Scheme 1.

In Scheme 1,3,6-dichloro-4,5-dimethylpyridazine (1) is displaced with a mono-boc protected substituted piperazine (2) in a nucleophilic aromatic substitution reaction (SNAr) to provide a 3-chloro-4,5-dimethyl-6-(substituted) pyridazine of formula (3). For example, in Step 1, a chloride of (1) can be reacted with a substituted mono boc protected piperazine in a polar aprotic solvent such as DMSO in the presence of an organic base such as diisopropylethylamine. In Step 2, the remaining chloride on the dimethylpyridazine (3) can be reacted with a phenyl boronic acid (4) in a Suzuki-Miyaura cross coupling reaction to give the corresponding 4,5-dimethyl-6-substituted phenylpyridazine-3-substituted piperazine (5). The skilled artisan will recognize that there are a variety of conditions useful for facilitating such cross-coupling reactions. The reaction conditions make use of a suitable solvent such as dioxane or dioxane/water and are accomplished in the presence of a base such as cesium fluoride. The reaction takes place in the presence of a palladium catalyst such as (1,1'-bis(diphenylphosphino)ferrocene)palladium(II) chloride, under an inert atmosphere at a temperature of about 80-160° C. to give a compound of formula (5). The amine can be deprotected by standard deprotection methods. Methods for introducing and removing nitrogen protecting groups are well known in the art (see, e.g., Greene and Wuts, *Protective Groups in Organic Synthesis*, 3$^{rd}$ Ed., John Wiley and Sons, New York, (1999)). For example, boc deprotection of the piperazine of formula (5) can be accomplished under acidic conditions, such as hydrogen chloride in a suitable solvent such as methanol or dioxane to give a compound of formula (6). Acylation of the amine in Step 4 can be accomplished with a substituted trichloroethyl carbamate (7) using an organic base such as triethylamine in a polar aprotic solvent such as DMSO and heating to about 90-110° C. Compounds of Formula I can be converted to a salt such as the HCl salt by methods known to one skilled in the art such as adding HCl in Et$_2$O to give compounds of Formula I.

The substituted trichloroethyl carbamate can be prepared as shown in Scheme 2.

Scheme 2

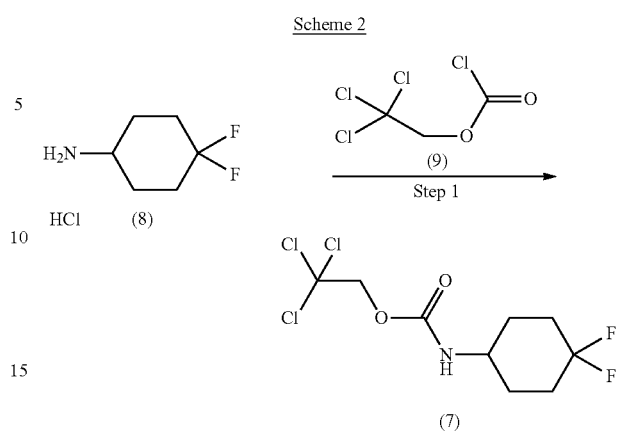

4,4-difluorocyclohexylamine hydrochloride (8) is acylated with 2,2,2-trichloroethyl carbonochloridate (9) using an organic base such as triethylamine in an inert solvent such as dichloromethane to give 2,2,2-trichloroethyl 4,4-difluorocyclohexylcarbamate, (7), Step 1.

Alternatively, 3,6-dichloro-4,5-dimethylpyridazine can be alkylated with benzyl ethylenediamine which can be elaborated to the cyclized piperazine as shown in Scheme 3.

Scheme 3

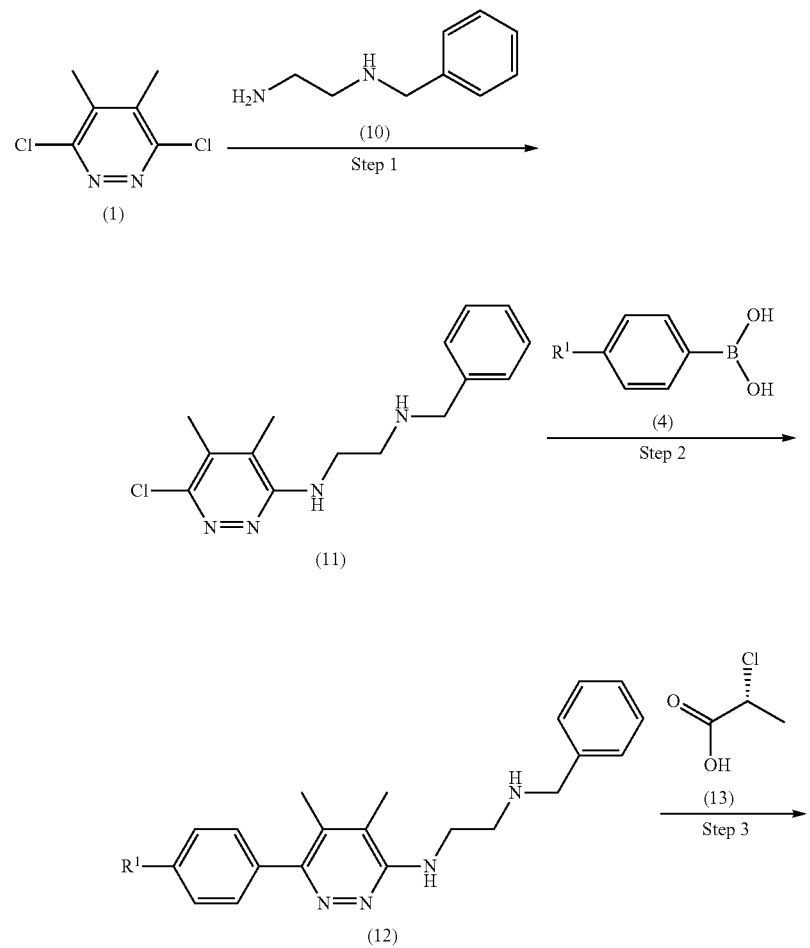

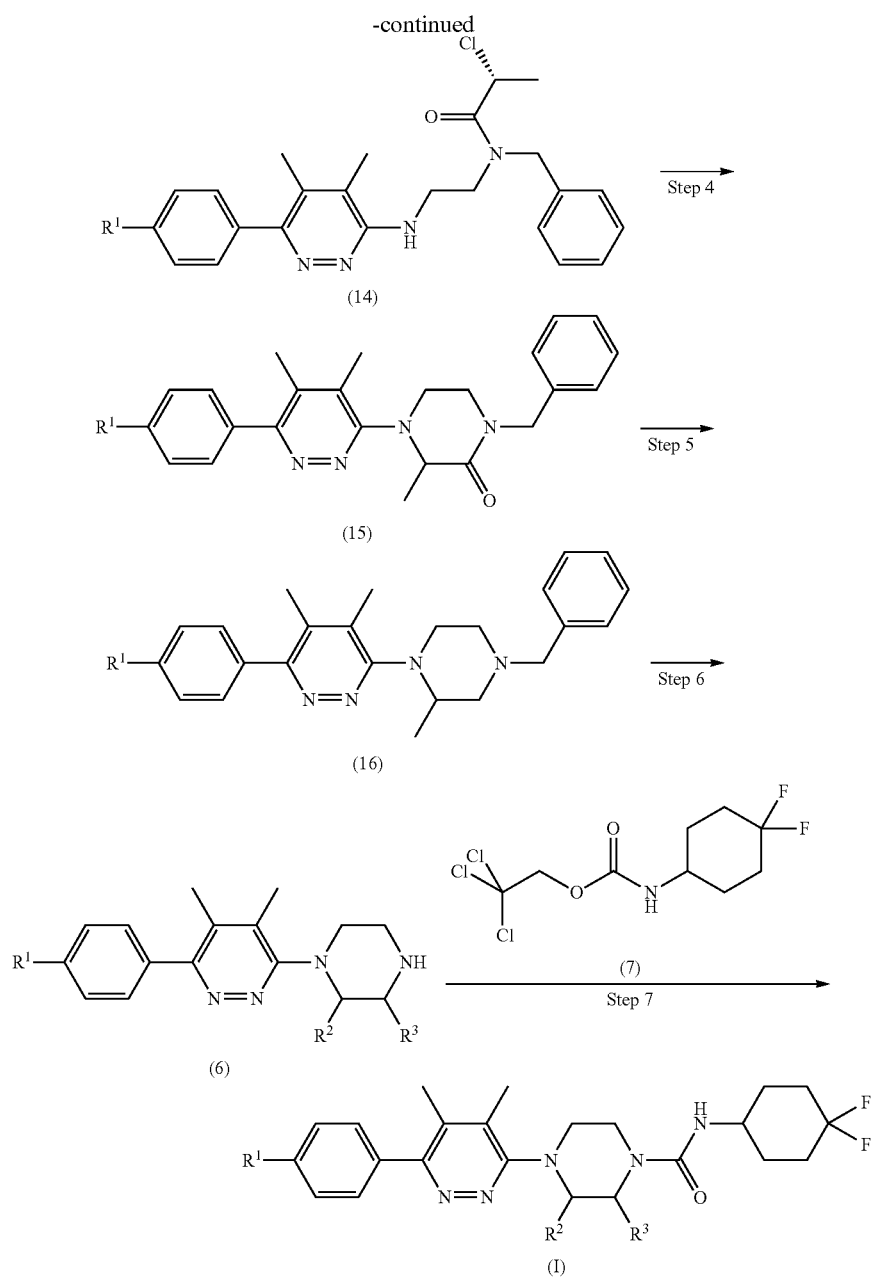

A chloride of (1) can be displaced with benzylethylenediamine (10) using an organic base such as diisopropylamine in a polar aprotic solvent such as DMSO with heating at 110-130° C. as shown in Step 1, Scheme 3 to give the protected ethylenediamine pyridazine of formula (11). The second chloride can be reacted as described earlier with a boronic acid (4) shown in Step 2 to give a compound of formula (12). The benzyl nitrogen is acylated with 2-chloropropionic acid (13) using an organic base such as triethylamine and a suitable coupling reagent such as EDCI with HOBT to give a compound of formula (14) as shown in Step 3. Cyclization to form the pyridazine is accomplished with sodium hydride in an inert solvent such as THF to give a compound of formula (15), Step 4. A reducing agent such as borane-methyl sulfide reduces the ketone to give a compound of formula (16), Step 5. For example, a compound of formula (15) can be treated with borane-methyl sulfide complex in an inert solvent such as THF. The mixture can be heated to 40-60° C. to give the substituted piperazine of formula (16). Deprotection of the piperizine is accomplished, under hydrogenation conditions of 40-70 psi hydrogen gas with a catalyst such as 10% Pd/C using a polar solvent such as ethanol to give a compound of formula (6), Step 6. Acylation of the amine in Step 7 can be accomplished with a substituted trichloroethyl carbamate (7) using an organic base such as triethylamine in a polar aprotic solvent such as DMSO and heating to about 90-110° C. to give compounds of Formula I which can be converted to a salt such as the HCl salt by methods known to one skilled in the art such adding HCl in Et$_2$O.

The following Preparations and Examples are provided to illustrate the invention in further detail and represent typical syntheses of the compounds of Formula I. The names of the compounds of the present invention are generally provided by ChemDraw Ultra® 10.0.

Preparation 1

(S)-tert-Butyl 4-(6-chloro-4,5-dimethylpyridazin-3-yl)-2-methylpiperazine-1-carboxylate

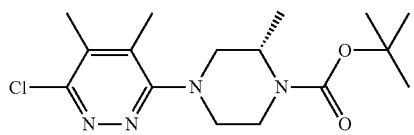 [SMILES: Cc1c(Cl)nnc(N2CCN(C(=O)OC(C)(C)C)[C@@H](C)C2)c1C]

Heat a mixture of 1,4-dichloro-2,3-dimethylpyridazine (6.06 g, 34.2 mmol), (S)-2-methyl-piperazine-1-carboxylic acid tert-butyl ester (6.88 g, 34.4 mmol) and diisopropylethylamine (30 ml, 172 mmol) in DMSO (30 mL) at 120° C. for 5 d. Cool and treat the mixture with additional (S)-2-methyl-piperazine-1-carboxylic acid tert-butyl ester (3.74 g, 18.7 mmol), and resume heating at 120° C. for an additional 2 d. Dilute the reaction mixture with EtOAc and wash with $H_2O$ and brine. Dry over $Na_2SO_4$, filter, and concentrate under reduced pressure. Purify the residue by flash silica gel chromatography (gradient of 20 to 50% EtOAc in hexanes) to afford the title compound as a pale yellow foam (7.36 g, 63%). ES/MS m/z ($^{35}$Cl) 341.0 (M+1).

Preparation 2

(S)-tert-Butyl 4-(4,5-dimethyl-6-phenylpyridazin-3-yl)-2-methylpiperazine-1-carboxylate

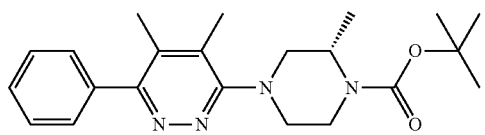

Treat a $N_2$ degassed mixture of (S)-tert-butyl 4-(6-chloro-4,5-dimethylpyridazin-3-yl)-2-methylpiperazine-1-carboxylate (3.03 g, 8.87 mmol), phenylboronic acid (1.62 g, 13.3 mmol), and CsF (4.09 g, 26.9 mmol) in 1,4-dioxane (120 mL) with (1,1'-bis(diphenylphosphino)ferrocene)palladium(II) chloride (1.08 g, 1.32 mmol). Heat the reaction mixture at 95° C. overnight. Cool the reaction, and partition between EtOAc and $H_2O$. Wash the organic layer with brine, dry over $Na_2SO_4$, filter, and concentrate under reduced pressure. Purify the residue by flash silica gel chromatography (gradient of 15 to 85% EtOAc in hexanes) to afford the title compound as a white solid (2.93 g, 86%). ES/MS m/z 383.0 (M+1).

Prepare the substituted dimethylpyridazines in the table below by essentially following the procedure described in Preparation 2, using the appropriate phenylboronic acid.

| Prep. No. | Chemical Name | Structure | ES/MS m/z |
|---|---|---|---|
| 3 | (S)-tert-Butyl 4-(6-(4-cyanophenyl)-4,5-dimethylpyridazin-3-yl)-2-methylpiperazine-1-carboxylate | 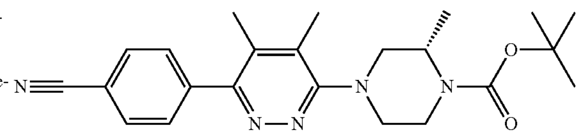 | 408.2 (M + 1) |
| 4 | (S)-tert-Butyl 4-(6-fluoro-4,5-dimethylpyridazin-3-yl)-2-methylpiperazine-1-carboxylate | 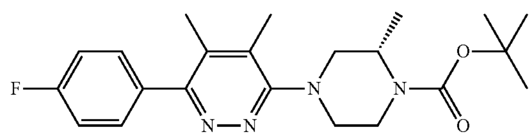 [SMILES: Cc1c(-c2ccc(F)cc2)nnc(N2CCN(C(=O)OC(C)(C)C)[C@@H](C)C2)c1C] | 400.8 (M + 1) |

Preparation 5

(S)-4,5-Dimethyl-3-(3-methylpiperazin-1-yl)-6-phenylpyridazine

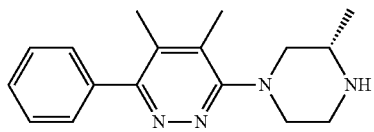 [SMILES: Cc1c(-c2ccccc2)nnc(N2CCN[C@@H](C)C2)c1C]

Treat a solution of (S)-tert-butyl 4-(4,5-dimethyl-6-phenylpyridazin-3-yl)-2-methylpiperazine-1-carboxylate (2.93 g, 7.66 mmol) in MeOH (20 mL) with 4 M HCl in 1,4-dioxane (10 mL, 40.0 mmol). Stir the reaction mixture at ambient temperature overnight. Concentrate the reaction mixture under reduced pressure. Dissolve the residue in MeOH, and pour onto an SCX column (Varian, 10 g). Rinse the column with MeOH. Elute the desired product with 2M $NH_3$/MeOH. Concentrate under reduced pressure to afford the title compound (2.07 g, 95%). ES/MS m/z 283.0 (M+1).

Prepare the deprotected piperazines in the table below by essentially following the procedure described in Preparation 5, using the appropriate boc-protected piperazine with reaction times of 3 h and using 1,4-dioxane instead of MeOH as the solvent.

| Prep. No. | Chemical Name | Structure | ES/MS m/z |
|---|---|---|---|
| 6 | (S)-4,5-Dimethyl-6-(3-methylpiperazin-1-yl)pyridazine-3-carbonitrile | 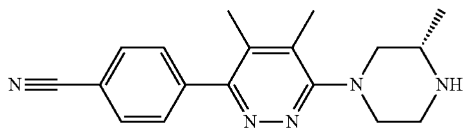 [SMILES: Cc1c(-c2ccc(C#N)cc2)nnc(N2CCN[C@@H](C)C2)c1C] | 308.2 (M + 1) |
| 7 | (S)-3-(4-Fluorophenyl)-4,5-dimethyl-6-(3-methylpiperazin-1-yl)pyridazine | 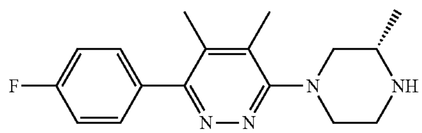 [SMILES: Cc1c(-c2ccc(F)cc2)nnc(N2CCN[C@@H](C)C2)c1C] | 301.2 (M + 1) |

Preparation 8

N1-Benzyl-N2-(6-chloro-4,5-dimethylpyridazin-3-yl)ethane-1,2-diamine

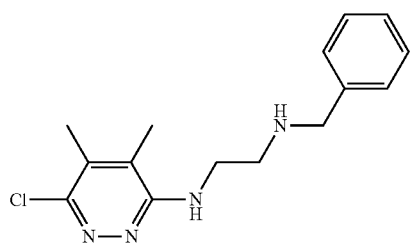 [SMILES: Cc1c(Cl)nnc(NCCNCc2ccccc2)c1C]

Heat a mixture of 3,6-dichloro-4,5-dimethylpyridazine (6.90 g, 39.0 mmol), N-benzylethylenediamine (8.78 g, 58.5 mmol), and diisopropylethylamine (25.2 g, 195 mmol) in DMSO (78 mL) at 120° C. for 3 d. Cool the reaction mixture, pour into H₂O, and extract the mixture with Et₂O. Wash the organic layer with H₂O, dry over Na₂SO₄, filter, and concentrate under reduced pressure. Purify the residue using flash silica gel chromatography (gradient of 0 to 5% 2 M NH₃/MeOH in CH₂Cl₂) to obtain the title compound as a waxy solid (6.41 g, 57%). ES/MS m/z 291.2 (M+1).

Preparation 9

N1-Benzyl-N2-(6-(4-fluorophenyl)-4,5-dimethylpyridazin-3-yl)ethane-1,2-diamine

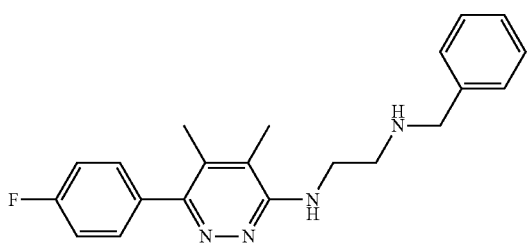 [SMILES: Cc1c(NCCNCc2ccccc2)nnc(-c2ccc(F)cc2)c1C]

Treat a N₂ degassed mixture of N1-benzyl-N2-(6-chloro-4,5-dimethylpyridazin-3-yl)ethane-1,2-diamine (6.40 g, 22.0 mmol), 4-fluorophenylboronic acid (9.24 g, 66.0 mmol) and CsF (10.0 g, 66.0 mmol) in 1,4-dioxane (220 mL) with (1,1'-bis(diphenylphosphino)ferrocene)palladium(II) chloride (2.70 g, 3.30 mmol). Heat the reaction mixture at 95° C. overnight. Cool, and partition between saturated NaHCO₃ (aq) and EtOAc. Separate the layers, and extract the aqueous layer with EtOAc. Combine the organic layers, dry over Na₂SO₄, filter, and concentrate under reduced pressure. Purify the residue by flash silica gel chromatography (gradient of 0 to 6% 2M NH₃/MeOH in CH₂Cl₂) to afford the title compound as a waxy solid (4.91 g, 64%). ES/MS m/z 351.2 (M+1).

Preparation 10

(R)—N-Benzyl-2-chloro-N-(2-(6-(4-fluorophenyl)-4,5-dimethylpyridazin-3-ylamino)ethyl)propanamide

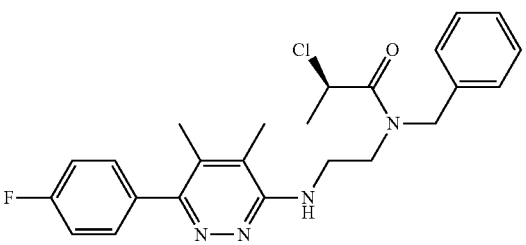 [SMILES: Cc1c(NCCN(Cc2ccccc2)C(=O)[C@@H](C)Cl)nnc(-c2ccc(F)cc2)c1C]

Sequentially treat a solution of N1-benzyl-N2-(6-(4-fluorophenyl)-4,5-dimethylpyridazin-3-yl)ethane-1,2-diamine (4.90 g, 13.98 mmol) in CH₂Cl₂ (70 mL) with (R)-(+)-2-chloropropionic acid (1.84 mL, 20.97 mmol), triethylamine (2.92 mL, 20.97 mmol), HOBT (3.21 g, 20.97 mmol), and 1-(3-dimethylaminopropyl)-3-ethylcarbodiimide hydrochloride (4.02 g, 20.97 mmol). Stir the resulting mixture at ambient temperature overnight. Wash the reaction mixture with saturated aqueous NaHCO₃. Extract the aqueous layer with CH₂Cl₂. Combine the organic layers, dry over Na₂SO₄, filter, and concentrate under reduced pressure. Purify the residue by flash silica gel chromatography (20% EtOAc in hexanes) to afford the title compound as a yellow foam (4.59 g, 74%). ES/MS m/z 441.2 (M+1).

Preparation 11

1-Benzyl-4-(6-(4-fluorophenyl)-4,5-dimethylpyridazin-3-yl)-3-methylpiperazin-2-one

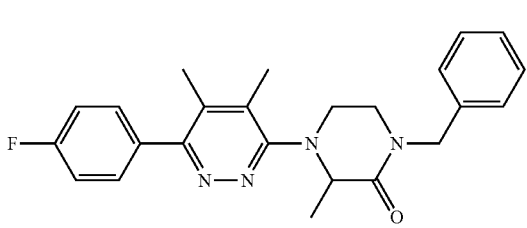 [SMILES: Cc1c(-c2ccc(F)cc2)nnc(N2CCN(Cc3ccccc3)C(=O)C2C)c1C]

Treat a 0° C. solution of (R)—N-benzyl-2-chloro-N-(2-(6-(4-fluorophenyl)-4,5-dimethylpyridazin-3-ylamino)ethyl)propanamide (4.59 g, 10.4 mmol) in THF (104 mL) with NaH (60%, 625 mg, 15.6 mmol). Allow the reaction mixture to warm to ambient temperature and stir overnight. Cool the reaction to 0° C., and treat with additional NaH (60%, 208 mg, 5.20 mmol). Allow the reaction mixture to warm to ambient temperature and stir for 3 d. Partition the reaction mixture between brine and EtOAc. Separate the organic layer, dry over $Na_2SO_4$, filter, and concentrate under reduced pressure. Purify the residue by flash silica gel chromatography (gradient of 0 to 2% 2 M $NH_3$/MeOH in $CH_2Cl_2$) to provide the title compound as a white foam (3.64 g, 86%). ES/MS m/z 405.2 (M+1).

Preparation 12

3-(4-Benzyl-2-methylpiperazin-1-yl)-6-(4-fluorophenyl)-4,5-dimethylpyridazine

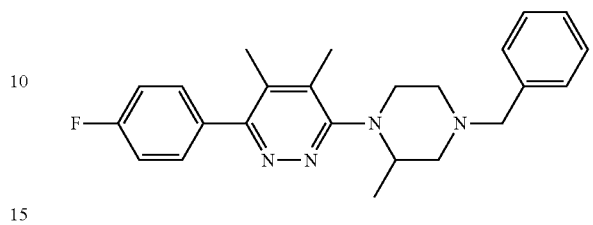

Treat a solution of 1-benzyl-4-(6-(4-fluorophenyl)-4,5-dimethylpyridazin-3-yl)-3-methylpiperazin-2-one (2.84 g, 7.02 mmol) in THF (70 mL) with borane-methyl sulfide complex (1.96 mL, 21.1 mmol). Heat the resulting mixture at 50° C. for 2 h. Cool the reaction mixture in an ice bath, add MeOH (20 mL) via a dropping funnel followed by 4 M HCl in 1,4-dioxane (20 mL). Heat the resulting mixture at 65° C. for 1 h. Concentrate the mixture under reduced pressure. Partition the residue between $CH_2Cl_2$ and saturated $NaHCO_3$ (aq). Separate the layers, and extract the aqueous layer with $CH_2Cl_2$. Combine the organic layers, dry over $Na_2SO_4$, filter, and concentrate under reduced pressure. Purify the residue by flash silica gel chromatography (gradient of 0 to 3% 2 M $NH_3$/MeOH in $CH_2Cl_2$) to afford the title compound as a waxy solid (2.45 g, 89%). ES/MS m/z 391.2 (M+1).

Separate the isomers of 3-(4-benzyl-2-methylpiperazin-1-yl)-6-(4-fluorophenyl)-4,5-dimethylpyridazine by chiral chromatography (Chiralcel OJ-H, flow rate 30 mL/min, detection 225 nm, 6:4 MeOH:acetonitrile). First eluting peak, Isomer 1: 99% ee. Second eluting peak, Isomer 2: 99% ee.

| Prep. No | Chemical Name | Structure | ES/MS m/z |
|---|---|---|---|
| 13 | 3-(4-Benzyl-2-methylpiperazin-1-yl)-6-(4-fluorophenyl)-4,5-dimethylpyridazine, Isomer 1 | 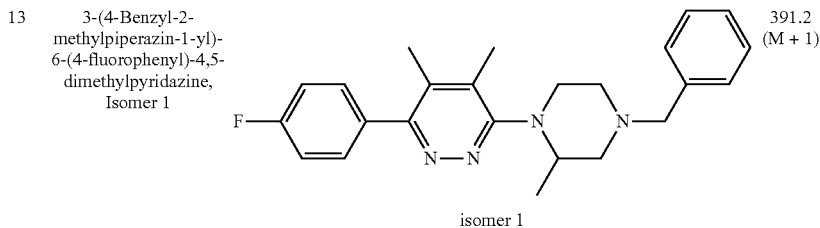 isomer 1 | 391.2 (M + 1) |
| 14 | 3-(4-Benzyl-2-methylpiperazin-1-yl)-6-(4-fluorophenyl)-4,5-dimethylpyridazine, Isomer 2 | 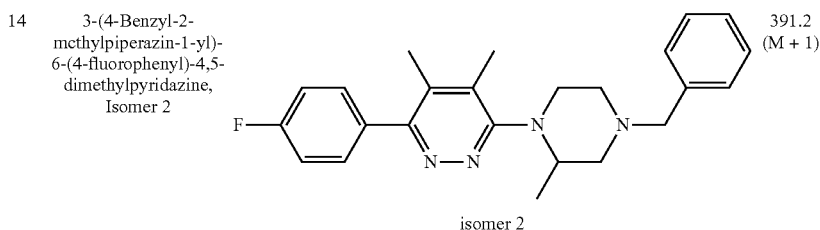 isomer 2 | 391.2 (M + 1) |

Preparation 15

3-(4-Fluorophenyl)-4,5-dimethyl-6-(2-methylpiperazin-1-yl)pyridazine

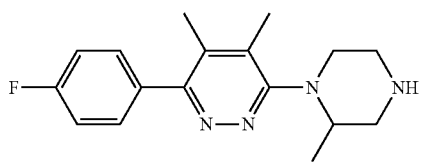 [SMILES: Cc1c(-c2ccc(F)cc2)nnc(N2CCNCC2C)c1C]

Add a solution of 3-(4-benzyl-2-methylpiperazin-1-yl)-6-(4-fluorophenyl)-4,5-dimethylpyridazine (200 mg, 3.25 mmol) in absolute EtOH (15 mL) to 10% Pd/C (46.8 mg) pre-wetted with EtOH (5 mL). Shake the mixture in a Parr bottle pressurized with $H_2$ at 60 psi for 10 h. Filter the reaction mixture, and apply the solution directly to an SCX column (Varian, 2 g). Rinse the column with MeOH and $CH_2Cl_2$. Elute the product with a 1:1 mixture of 2 M $NH_3$/MeOH and $CH_2Cl_2$. Concentrate the eluent under reduced pressure to afford the title compound as an off-white foam (142 mg, 92%). ES/MS m/z 301.2 (M+1).

Prepare the deprotected methyl piperazines in the following table by following the procedure described in Example 15, using the appropriate protected amine.

mL, 42.2 mmol) in $CH_2Cl_2$ (192 mL) with 2,2,2-trichloroethyl carbonochloridate (2.91 mL, 21.1 mmol) dropwise. After 1 h, allow the reaction mixture to warm to ambient temperature and stir overnight. Partition the reaction mixture between $H_2O$ and $CH_2Cl_2$ and separate the layers. Dry the organic layer over $Na_2SO_4$, filter, and concentrate under reduced pressure to provide the title compound as an off-white solid (5.75 g, 97%). GC/MS m/z $^{35}$Cl 309 (M+).

EXAMPLE 1

(S)—N-(4,4-Difluorocyclohexyl)-4-(4,5-dimethyl-6-phenylpyridazin-3-yl)-2-methylpiperazine-1-carboxamide hydrochloride

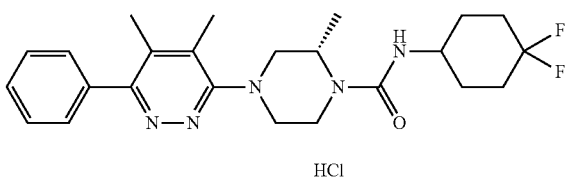

Treat a mixture of (S)-4,5-dimethyl-3-(3-methylpiperazin-1-yl)-6-phenylpyridazine (199 mg, 0.70 mmol) and triethy-

| Prep. No | Chemical Name | Structure | ES/MS m/z |
|---|---|---|---|
| 16 | 3-(4-Fluorophenyl)-4,5-dimethyl-6-(2-methylpiperazin-1-yl)pyridazine | isomer 1 | 301.2 (M + 1) |
| 17 | 3-(4-Fluorophenyl)-4,5-dimethyl-6-(2-methylpiperazin-1-yl)pyridazine | isomer 2 | 301.2 (M + 1) |

Preparation 18

2,2,2-Trichloroethyl 4,4-difluorocyclohexylcarbamate

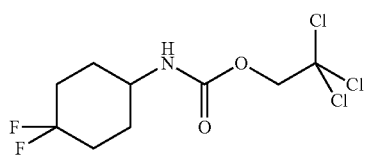 [SMILES: O=C(NC1CCC(F)(F)CC1)OCC(Cl)(Cl)Cl]

Treat a 0° C. mixture of 4,4-difluorocyclohexylamine hydrochloride (3.29 g, 19.2 mmol) and triethylamine (5.88 lamine (0.30 ml, 2.15 mmol) in DMSO (5 ml) with 2,2,2-trichloroethyl 4,4-difluorocyclohexylcarbamate (341 mg, 1.10 mmol). Heat the reaction at 100° C. for 4 d. Pour the reaction mixture into $H_2O$, rinsing with EtOAc. Extract the mixture with EtOAc. Wash the organic layer twice with $H_2O$, then brine. Dry over $Na_2SO_4$ and concentrate under reduced pressure. Purify the resulting residue by flash silica gel chromatography (gradient of 0 to 10% MeOH in $CH_2Cl_2$). Dissolve the purified free base in MeOH (1 mL) and treat with 1 M HCl in $Et_2O$ (1 mL). Concentrate the mixture to provide the title compound as a yellow foam (256 mg, 76%). ES/MS m/z 444.2 (M+1).

Prepare the piperazinyl ureas in the table below by essentially following the procedure described in Example 1, using the appropriate piperazinylpyridazine.

| Ex. No. | Chemical Name | Structure | ES/MS m/z |
|---|---|---|---|
| 2 | (S)-N-(4,4-Difluorocyclohexyl)-4-(6-(4-fluorophenyl)-4,5-dimethylpyridazin-3-yl)-2-methylpiperazine-1-carboxamide hydrochloride | 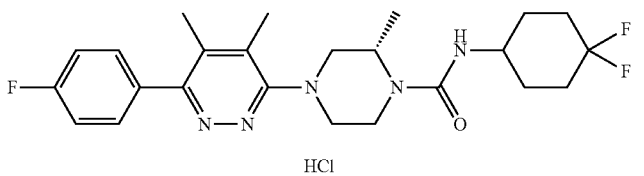 [SMILES: Cc1c(-c2ccc(F)cc2)nnc(N2CCN(C(=O)NC3CCC(F)(F)CC3)[C@@H](C)C2)c1C ; Cl] | 461.8 (M + 1) |
| 3 | (S)-4-(6-(4-Cyanophenyl)-4,5-dimethylpyridazin-3-yl)-N-(4,4-difluorocyclohexyl)-2-methylpiperazine-1-carboxamide hydrochloride | 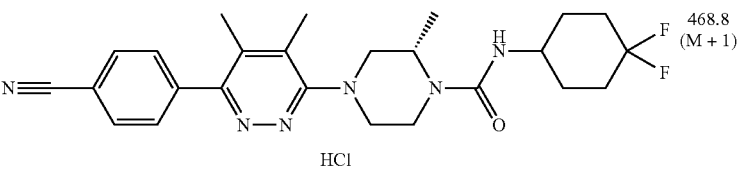 | 468.8 (M + 1) |
| 4 | N-(4,4-Difluorocyclohexyl)-4-(6-(4-fluorophenyl)-4,5-dimethylpyridazin-3-yl)-3-methylpiperazine-1-carboxamide hydrochloride | 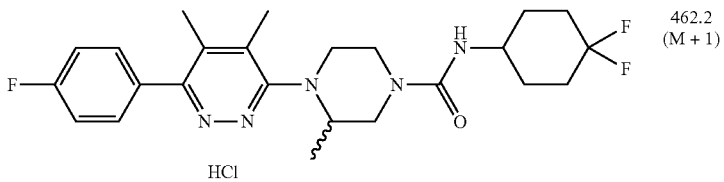 | 462.2 (M + 1) |
| 5 | N-(4,4-Difluorocyclohexyl)-4-(6-(4-fluorophenyl)-4,5-dimethylpyridazin-3-yl)-3-methylpiperazine-1-carboxamide hydrochloride, Isomer 1 | 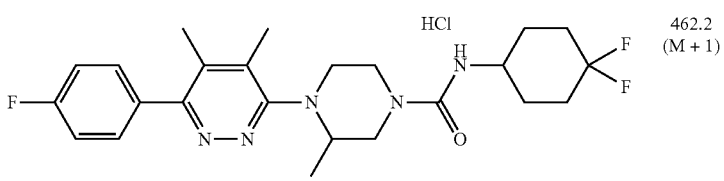 Isomer 1 | 462.2 (M + 1) |
| 6 | N-(4,4-Difluorocyclohexyl)-4-(6-(4-fluorophenyl)-4,5-dimethylpyridazin-3-yl)-3-methylpiperazine-1-carboxamide hydrochloride, Isomer 2 | 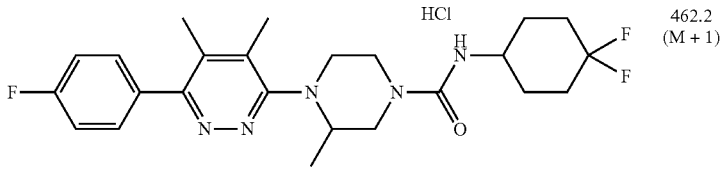 Isomer 2 | 462.2 (M + 1) |

Biology

Hedgehog has been implicated as a survival factor for the following cancers: basal cell carcinoma; upper gastro intestinal tract cancers (esophagus, stomach, pancreas, and biliary tract); prostate cancer; breast cancer; small cell lung cancer; non-small cell lung cancer; B-cell lymphoma; multiple myeloma; gastric cancer; ovarian cancer; colorectal cancer; liver cancer; melanoma; kidney cancer; and brain cancer.

Elements of the hedgehog pathway have been asserted to be potential drug targets for the treatment of cancers. A Daoy cell line established from medulloblastoma tumor (ATCC, HTB-186), is responsive to Hh ligands. When these cells are treated with exogenously added Shh-conditioned media, Hh signaling pathway is activated and results in an increased expression of Gli1. Cyclopamine, an alkaloid isolated from the corn lily *Veratrum californicum* is a weak hedgehog antagonist and has been shown to suppress the expression of Gli1 in response to Shh stimulation. Recent observations suggest that cyclopamine inhibits the growth of cultured medulloblastoma cells and allografts. Using this Daoy cell model system, potent inhibitors of hedgehog signaling pathways can be identified. Since the compounds of the present invention are hedgehog antagonists, they are suitable for treating the aforementioned tumor types.

Determination of Biological Activity $IC_{50}$

The following assay protocol and results thereof further demonstrate the utility and efficacy of the compounds and methods of the current invention. Functional assays provide support that the compounds of the present invention exhibit the ability to inhibit Shh signaling. All ligands, solvents, and reagents employed in the following assay are readily available from commercial sources or can be readily prepared by one skilled in the art.

Biological activity is determined using a functional assay in Daoy neuronal cancer cells and measures levels of Gli1 ribonucleic acid via a bDNA (branched deoxyribonucleic acid) assay system (Panomics, Inc., Fremont, Calif.). Gli was originally discovered in a Glioblastoma cell line and encodes a zinc finger protein that is activated by Shh signaling. The maximum response is obtained by inducing Gli1 transcription in the Daoy cells with conditioned medium (human embryonic kidney, HEK-293 cells stably expressing recombinant Shh) for 24 hours and then measuring the amount of stimulated Gli1 transcript. The minimum response is the amount of Gli1 transcript inhibited with a control compound in Daoy cells that have been stimulated with conditioned media (human embryonic kidney, HEK-293 cells stably expressing recombinant Shh) for 24 hours.

Functional Assay for Measuring the Inhibition of Gli1 in Daoy Cells

The bDNA assay system utilizes the technology of branched-chain DNA to allow amplification of a target ribonucleic acid (transcript). The technology employs three types of synthetic hybrid short Gli1-specific cDNA probes that determine the specificity of the target transcript [capture extenders (CEs), label extenders (LEs), and blockers (BLs)] that hybridize as a complex with the target transcripts to amplify the hybridization signal. The addition of a chemilumigenic substrate during the amplification step allows for detection using luminescence.

The Daoy cell line obtained from American Type Culture collection (ATCC) is a Shh-responsive human neuronal tumor cell line and was established in 1985 from a desmoplastic cerebellar medullablastoma tumor, a physiologically relevant tumor cell line. Endogenous levels of Gli1 transcripts levels are low in Daoy cells but can be stimulated by using conditioned media taken from cells stably over-expressing human Shh (a HEK-293 cell line stably transfected with hShh).

Daoy cells are grown to confluency in tissue culture T225-flasks in Daoy growth media containing Minimum Essential Medium (MEM) plus 10% Fetal Bovine Serum (FBS) with 0.1 nM non-essential amino acids and 1 mM sodium pyruvate. The cells are removed from the T225-flasks using trypsin ethylenediaminetetraacetic acid (EDTA), centrifuged, resuspended in media, and then counted.

The Daoy cells are then seeded at 50,000 cells per well in growth media in Costar 96 well clear tissue culture plates and allowed to incubate overnight at 37° C. under 5% carbon dioxide ($CO_2$). The cells are washed one time in phosphate buffered saline (PBS) followed by addition of 100 µL, of Shh Conditioned Media (Shh-CM) to stimulate levels of Gli1 expression. Shh-CM is diluted to achieve maximum stimulation using control growth media—0.1% FBS/DMEM (Dulbeccos Modified Eagle Medium). Daoy cells treated with Shh-CM are then treated with various concentrations of hedgehog inhibitors ranging from approximately 1 µM to 0.1 nM. Test compounds are allowed to incubate for 24 hours at 37° C. under 5% $CO_2$.

The measurement of the Gli1 transcript is performed by using the Quantigene 2.0 Gli1 assay as described by the manufacturer (Panomics, Inc.). Prepare a diluted lysis mixture (DLM) buffer, which includes Proteinase K. After a 24 hour incubation with compound, the cells are washed one time with PBS and 180 µL, of DLM is added to the cells. The cell plate containing the lysis buffer is sealed and placed at 55° C. for 30 to 45 minutes. The resulting cell lysates are then triturated 5 times. A working probe set containing Gli1 probes is made by diluting the probes in the DLM according to the manufacturer's directions, and then 20 µL, of the working probe set is added to the bDNA assay plates along with 80 µL, of the Daoy lysates. The plates are sealed and incubated overnight at 55° C. The bDNA plates are then processed according to the manufacturer's directions. The signal is quantified by reading the plates on a Perkin Elmer Envision reader detecting luminescence. The luminescent signal is directly proportional to the amount of target transcript present in the sample.

The luminescent signal data from the functional assay are used to calculate the $IC_{50}$ for the in vitro assay. The data are calculated based on the maximum control values (Daoy cells treated with Shh-CM) and the minimum control value (Daoy cells treated with Shh-CM and an inhibitory concentration of a control compound, 1 µM of N-(3-(1H-benzo[d]imidazol-2-yl)-4-chlorophenyl)-3,5-dimethoxybenzamide). A four parameter logistic curve fit is used to generate the $IC_{50}$ values using ActivityBase software programs version 5.3, equation 205 (*Assay Guidance Manual Version* 5.0, 2008, Eli Lilly and Company and NIH Chemical Genomics Center).

Following the protocol described, the compounds of the invention exemplified herein display an $IC_{50}$ of <15 nM. For example, the compound of Example 1 has an $IC_{50}$ of approximately 1.26 nM with a standard error of 0.139 (n=3) in the assay described above. These results provide evidence that the compounds of the present invention are hedgehog antagonists and, as such, are useful as anticancer agents.

We claim:

1. A compound of the following formula:

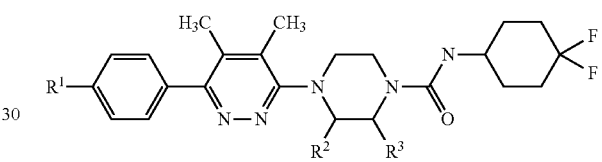

wherein:
$R^1$ is hydrogen, fluoro or cyano; and
$R^2$ and $R^3$ are independently methyl or hydrogen;
or a pharmaceutically acceptable salt thereof.

2. The compound of claim 1 wherein $R^1$ is hydrogen, or a pharmaceutically acceptable salt thereof.

3. The compound of claim 1 wherein one of $R^2$ and $R^3$ is hydrogen and the other is methyl, or a pharmaceutically acceptable salt thereof.

4. The compound according to claim 3 wherein $R^1$ is hydrogen, $R^2$ is hydrogen and $R^3$ is methyl, or a pharmaceutically acceptable salt thereof.

5. A pharmaceutical composition comprising a compound of claim 1, or a pharmaceutically acceptable salt thereof, in combination with a pharmaceutically acceptable carrier, diluent or excipient.

6. A compound according to claim 4 which is (S)—N-(4,4-difluorocyclohexyl)-4-(4,5-dimethyl-6-phenylpyridazin-3-yl)-2-methylpiperazine-1-carboxamide, or a pharmaceutically acceptable salt thereof.

7. The compound according to claim 6 which is (S)—N-(4,4-difluorocyclohexyl)-4-(4,5-dimethyl-6-phenylpyridazin-3-yl)-2-methylpiperazine-1-carboxamide hydrochloride.

8. A pharmaceutical composition comprising a compound according to claim 6, or a pharmaceutically acceptable salt thereof, in combination with a pharmaceutically acceptable carrier, diluent or excipient.

9. A pharmaceutical composition comprising a compound according to claim 7, in combination with a pharmaceutically acceptable carrier, diluent or excipient.

* * * * *